(12) United States Patent  (10) Patent No.: US 9,334,532 B2
Seitz et al.  (45) Date of Patent: May 10, 2016

(54) COMPLEXITY REDUCTION METHOD

(75) Inventors: Alexander Seitz, Vienna (AT); Jakob Haglmüller, Vienna (AT); Torsten Reda, Vienna (AT)

(73) Assignee: LEXOGEN GMBH (AT)

( * ) Notice: Subject to any disclaimer, the term of this patent is extended or adjusted under 35 U.S.C. 154(b) by 137 days.

(21) Appl. No.: 13/522,951

(22) PCT Filed: Feb. 2, 2011

(86) PCT No.: PCT/EP2011/051442
§ 371 (c)(1),
(2), (4) Date: Jul. 18, 2012

(87) PCT Pub. No.: WO2011/095501
PCT Pub. Date: Aug. 11, 2011

(65) Prior Publication Data
US 2012/0289412 A1  Nov. 15, 2012

(30) Foreign Application Priority Data

Feb. 3, 2010 (EP) .................................... 10152498

(51) Int. Cl.
*C12Q 1/68* (2006.01)
(52) U.S. Cl.
CPC ............ *C12Q 1/6855* (2013.01); *C12Q 1/6869* (2013.01)
(58) Field of Classification Search
None
See application file for complete search history.

(56) References Cited

U.S. PATENT DOCUMENTS 5,876,932 A * 3/1999 Fischer ................. 435/6.18
2005/0100911 A1 * 5/2005 Patil et al. ................ 435/6

FOREIGN PATENT DOCUMENTS

| WO | 2006137734 A1 | 12/2006 |
| WO | 2007073171 A2 | 6/2008 |
| WO | 2008093098 A2 | 8/2008 |
| WO | 2009073629 A2 | 6/2009 |
| WO | 2009116863 A2 | 9/2009 |

OTHER PUBLICATIONS

Prashar et.al., Analysis of differential gene expression by display of 3' end restriction fragments of cDNA, PNAS, Jan. 1996, vol. 93, pp. 659-663).*

* cited by examiner

*Primary Examiner* — Stephanie K Mummert
(74) *Attorney, Agent, or Firm* — Wagenknecht IP Law Group PC

(57) ABSTRACT

A method for the reduction of the complexity of nucleic acid pool(s), comprising: providing a sample with one or more nucleic acid molecules; cutting the nucleic acid molecules by a random and/or sequence independent cutting step thereby obtaining a pool of nucleic acid fragments; and amplifying one or more fragments of said nucleic acid molecules, wherein the one or more fragments constitute at least a fraction of all fragments of the nucleic acid molecules, wherein the amplified or amplifying one or more fragments of said fraction are divided into different subpools, and wherein the fragments of each subpool comprise a common nucleic acid feature.

18 Claims, 5 Drawing Sheets

1. Obtaining a pool of potentially different polynucleotides

2. Random Fragmentation of the polynucleotides of the pool

3. Ordering the pool of fragments into n specific subpools by subpool specific selective amplification subpool 1:

subpool 2:

subpool 3:

subpool n:

Fig. 3A

1. Obtaining a pool of potentially different polynucleotides

2. Random fragmentation of the polynucleotides of the pool

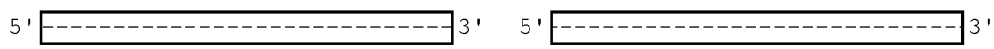

3. Linking of 5' and 3' linkers to the fragments of the pool

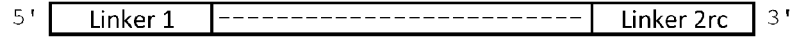

4. Selective amplification of subpools during PCR using the pool of fragments as a template

subpool 1: 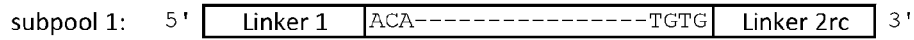
subpool 2: 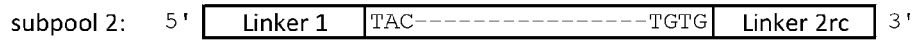
subpool 3: 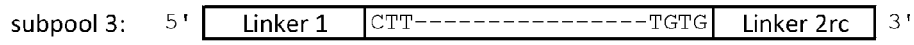

subpool 8: 
subpool 9: 

subpool 70: 

5. Fragmentation of the polynucleotides in each of the individual subpools

subpool 1: 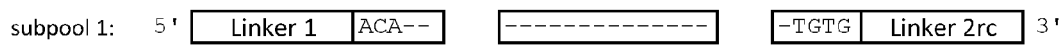

subpool 70: 

9. Determining the polynucleodide sequences by assembling sequences in each subpool

SEQUENCE LISTING

<160> NUMBER OF SEQ ID NOS: 10

<210> SEQ ID NO 1
<211> LENGTH: 202
<212> TYPE: DNA
<213> ORGANISM: Artificial Sequence
<220> FEATURE:
<223> OTHER INFORMATION: random sequence

<400> SEQUENCE: 1
cattacgtcc atatgagttc acggtccctt gaacttttat ggtaggtggt aggctcggcg      60
aatctagctt tggagcttcg ccggactcaa caaggtaagg aggagcatcg ctctctcgac     120
cactcaagac gggatattac ttgtgtcaag gagataatcg gaactattct ttagaatcca     180
gctcgccgaa atcgtcaggc ga                                              202

<210> SEQ ID NO 2
<211> LENGTH: 242
<212> TYPE: DNA
<213> ORGANISM: Artificial Sequence
<220> FEATURE:
<223> OTHER INFORMATION: random sequence

<400> SEQUENCE: 2

```
ctagcttcgg tgtcatcccg gaaggcccac gttgtgcggc aatactagag ataaaagcgg      60
caaagctaac accgaaagcc tatactggct acccgtctcg ttcggtggca ctaactagac     120
tcctcatcag gcataggtga ccgctcgctc tcgtgccaag gtctcccgag acttccgaga     180
tagtaataac tgaacatgga gaccggtatt gttaagctac atcaattgtg ggcgaaacga     240
ac                                                                    242
```

<210> SEQ ID NO 3
<211> LENGTH: 275
<212> TYPE: DNA
<213> ORGANISM: Artificial Sequence
<220> FEATURE:
<223> OTHER INFORMATION: random sequence

<400> SEQUENCE: 3

```
cgttccggcc tgaagctcgg ggatccggcc cccccctaac ttcgctttct caaacgtaca      60
aatcaacctt actcgcatgc agtagatctg ctttgggccg tatcacacct tcggcttgcc     120
gtaaacctga atagcaaatg cgggagggac tttccgtaat gttgggaatt acttaaacac     180
atcttccggg agcacaattt tccgccactc aacacgggtt ttccttggtg cgtctcatgc     240
aattcttcag tgatgggata cttggcaggg atatc                                275
```

<210> SEQ ID NO 4
<211> LENGTH: 297
<212> TYPE: DNA
<213> ORGANISM: Artificial Sequence
<220> FEATURE:
<223> OTHER INFORMATION: random sequence

<400> SEQUENCE: 4

```
cagcccggac gcactgagat gatacgtgtt gaaccggcct tcactgtata ttatgctcac      60
gagccctaga ttcatcaaaa aacaggtaca cttctcatcc tgactataca gctttcagtc     120
atcctacgat gggaatctag agcccataga catatatgag cacactactc ttggtaacat     180
ctcttgtcac atacattcgc caatctgaat ccttttctga cagccagttc tcatgatcca     240
acacttaagg atttagcatt acggggcggg aggagaatcg aatactcgcc caccgtc       297
```

<210> SEQ ID NO 5
<211> LENGTH: 304
<212> TYPE: DNA
<213> ORGANISM: Artificial Sequence
<220> FEATURE:
<223> OTHER INFORMATION: random sequence

<400> SEQUENCE: 5

```
actggagagc accgaacata ctcctagccc gggatgacaa tgtcctaacg ccacccacta      60
agggtaaggc tctaattgga aggtagtcca aatacgctcc atgacgagct cgctctcaa     120 ggctcgcagt cagaacgtat cgactatgcg actctaattc caaacccaga acctgagcga     180
ggcagtcgtt agttaatgac gcttgccgag agaacagtaa aggagttctt cgatgaggta     240
ctacgacatt cacatgtgtc atgggtcggt taagcatctg cgtgattgat tccggggggg     300
tgtt                                                                  304
```

<210> SEQ ID NO 6
<211> LENGTH: 297
<212> TYPE: DNA

```
<213> ORGANISM: Artificial Sequence
<220> FEATURE:
<223> OTHER INFORMATION: random sequence

<400> SEQUENCE: 6
cagcaggtcg catatatcaa aagggaaagc cagctcgcct agacgtcgtt caatggtagg      60
tactttaatt tttagagggg cttccccatg cttttggaga ttggcctatc ggtagtgagg     120
ataccggcct ccacgctgcg tgatgagcac aatcattgtt ctcggagacg gaggacccgg     180
aaggtaacga gcccaaaggt cattcatacc atatagggcg taacctcatt tagcgcgact     240
gacgtgcaag gggcatccga cctgcgagga aggggccttg gctctgtagg atataat       297

<210> SEQ ID NO 7
<211> LENGTH: 275
<212> TYPE: DNA
<213> ORGANISM: Artificial Sequence
<220> FEATURE:
<223> OTHER INFORMATION: random sequence

<400> SEQUENCE: 7
tatcgaaagc cctaaggatt ttttttgggg aatcgattgt gttaagcagg gacggcttca      60
aaattcgtct aataagattc tctggccatt accctaacag cgccatactc tatagacgca     120
cgcctacctt aggcgcctcc cgtccccgga tccgagctcc caaaacccag cgacctcttc     180
atgctaagga cttcatttgg acccgtcagg cactgctcca tgaagaacga catgaggatt     240
tggagtatta aaggcttaac actgtagcgc caccg                               275

<210> SEQ ID NO 8
<211> LENGTH: 242
<212> TYPE: DNA
<213> ORGANISM: Artificial Sequence
<220> FEATURE:
<223> OTHER INFORMATION: random sequence

<400> SEQUENCE: 8
gtgtcgtaac tgagcgatac agaacgacgc tgagtcatcg aggcaaatgc gtccacccgc      60
acctgcgcat cccatacaag gtggcacaac ttagtaggac ttatatgcgg acttcaccgg     120
tacgagaaga gttgaagact aaattatgac gtgacaaacg aaagagtaaa acaacatgcg     180
tagctcttca tgaagcggca gagcaaacct tgattaaacc ccttgattgg caacactaca     240
cg                                                                   242

<210> SEQ ID NO 9
<211> LENGTH: 202
<212> TYPE: DNA
<213> ORGANISM: Artificial Sequence
<220> FEATURE:
<223> OTHER INFORMATION: random sequence

<400> SEQUENCE: 9
cggttacccg gcgttaggcc tatgtaccgc ccgacgtact tgctaggggt catactaccg      60
acgatccctg ctaacaaaga acagtaccgg cttcccttaa ctactcagtg ctactaaaac     120
tagcatgagg gttgagatca tctcatccag ttgggtccag cgcatgatta attgctttac     180
tcgcacttta attcggcttc ta                                             202

<210> SEQ ID NO 10
<211> LENGTH: 160
<212> TYPE: DNA
<213> ORGANISM: Artificial Sequence
```

```
<220> FEATURE:
<223> OTHER INFORMATION: random sequence

<400> SEQUENCE: 10
ggaggcacga cgagtatcta gtgtctgcac gggactccgg aggacattcc ctacaagtta      60
ccggcgtcag tagcagcaag actggtctgt ctaccctgc ctgacaaagt ctttcttgga     120
tttcggaccg aaactcggcc caacatgcca ttggccatat                          160
```

COMPLEXITY REDUCTION METHOD

CROSS REFERENCE TO RELATED APPLICATIONS

This is a national phase application under 35 U.S.C. §371 of international application serial no. PCT/EP2011/051442, filed Feb. 2, 2011, which claims priority to European patent application serial no. 10152498.1, filed Feb. 3, 2010; the contents of which are herein incorporated by reference.

TECHNICAL FIELD

The present invention relates to the field of analyzing complex mixtures of nucleic acids through sequencing, especially high throughput sequencing techniques, such as Next generation Sequencing (NGS).

BACKGROUND OF THE INVENTION

NGS is currently the foremost complete analyzing method. Next generation sequencing is a generic term for parallelized sequencing through polymerization as high-throughput DNA sequencing method. NGS reads sequences of up to many millions fragments which are typically between 10 to several hundred base-pairs long. The complete sequence is obtained by alignment of those reads which is a challenging task due to the sheer number of small reads that have to be assembled to a complete sequence. Some NGS methods rely on a consensus blue print held in genomic and/or transcriptomic databases. The quality of the results depends on length and number of reads, reading accuracy, quality of information in the reference database and applied bioinformatics algorithms. To date many reads provide just limited information. For instance many of the reads cannot be assigned uniquely and therefore are discarded.

In more detail, for generating detectable signals most NGS approaches must amplify individual DNA molecules. Emulsion polymerase chain reaction (PCR) isolates individual DNA molecules using primer-coated beads in aqueous bubbles within an oil phase. Singularizing of DNA molecules, e.g. by rigorous dilution is another option. Another method for in vitro clonal amplification is bridge PCR, where fragments are amplified upon primers attached to a solid surface. Another option is to skip this amplification step, directly fix DNA molecules to a surface. Such DNA molecules or above mentioned DNA coated beads are immobilized to a surface, and sequenced in parallel. Sequencing by synthesis, like the "old style" dye-termination electrophoretic sequencing, uses a DNA polymerase to determine the base sequence. Reversible terminator methods use reversible versions of dye-terminators, adding one nucleotide at a time, detecting fluorescence at each position by repeated removal of the blocking group to allow polymerization of another nucleotide. Pyrosequencing also uses DNA polymerization, adding one nucleotide species at a time and detecting and quantifying the number of nucleotides added to a given location through the light emitted by the release of attached pyrophosphates. The sequencing by ligation method uses a DNA ligase to determine the target sequence. Used in the polony method and in the SOLiD® technology, it employs a partition of all possible oligonucleotides of a fixed length, labeled according to the sequenced position. Oligonucleotides are annealed and ligated. The preferential ligation by DNA ligase for matching sequences results in a dinucleotide encoded colour space signal at that position.

NGS technologies are essentially based on random amplification of input DNA fragments. This simplifies preparation but the sequencing remains undirected. The sheer complexity of the complete sample information simultaneously obtained, is the key hindrance for unambiguous alignment of the reads. Therefore, complexity reduction is essential for increasing the quality of the results.

The classical route for genomic complexity reduction, i.a. employed during the human genome project, is to create BAC (bacterial artificial chromosome) clones prior to sequencing. Distinct stretches of genomic DNA are cloned into bacterial host cells, amplified, extracted and used as templates for Sanger sequencing. Production, maintenance and verification of large BAC libraries are laborious processes and associated with appreciable costs. Due to these impracticalities and the incompatibility with existing NGS platforms it is generally sought to avoid bacterial cloning.

Another option to reduce complexity is to first select polynucleic acids based on their respective sizes. Different approaches include, but are not limited to, agarose gel electrophoresis or size exclusion chromatography for fractionation.

Small RNA sequencing approaches employ this method in order to obtain e.g. a fraction of RNA molecules called micro RNA (miRNA) sized between 15 and 30 nucleotides.

The probably most straightforward approach of complexity reduction is by limiting the amount of input nucleic sample to the genomic DNA of a single cell. Single-cell sequencing approaches rely on amplification reactions from highly dilute solutions, are incapable of actually reducing the complexity inherent to cellular content and are based solely on a selection of the input cells.

A different method for reducing the amount of input nucleic acid to below the amount contained within a single cell sometimes is termed limited dilution. A genomic nucleic acid sample is sheared and diluted to an extent where spatial distribution of the nucleic acid fragments within the sample volume becomes significant. Then subpools are created by taking such small volumes from the total sample volume that most subpools contain no nucleic acids, a few subpools contain one nucleic acid each and even less subpools contain two nucleic acids. This leads to a singularization of nucleic acids and therefore to complexity reduction compared to the full length genome as each singularized nucleic acid is a fragment of a genome. Therefore an increased sequence assembly efficiency for the individual nucleic acid fragment containing subpools is gained. Assembly and scaffold building for large genomes thereby is facilitated. In transcription analysis such a limited dilution approach will not reduce complexity introduced through variations in expression of different genes as each transcript molecule will occupy one subpool and therefore as many subpools are needed as molecules in the sample to display the entire transcriptome of a sample.

A further option is to sequence-specifically reject RNA, e.g. in a hybridization-based approach that removes ribosomal RNA from the entire RNA sample. As opposed to other fractionation methods that rely either on prior sequence information or are directed towards a certain RNA fraction (e.g. polyA selection), removal of rRNA does not bias the sequencing sample. However, the mere removal of ribosomal RNA is restricted to RNA samples and cannot be scaled in terms of complexity reduction.

The duplex-specific nuclease (DSN) method can be used for selectively removing double stranded DNA from the sample solution. This is achieved by letting the single stranded sample interact with excess driver DNA. Driver DNA is made up of sequences designed to remove their targets from the original sample. Upon interaction duplexes are formed, degraded by DSN and the remaining sample may be used for subsequent sequencing. Normalization of sample concentrations may be achieved by amplification using "partial PCR suppression". This method is not "hypothesis neutral" as it requires preparation of PCR fragments as driver DNA, and therefore prior sequence information.

It is also possible to employ sequence-specific selection methods, e.g. by targeted sequencing of genomic regions such as particular exons. The idea behind such capture arrays is to insert a selection step prior to sequencing. Those arrays are programmed to capture only the genomic regions of interest and thus enabling users to utilize the full capacity of the NGS machines in the sequencing of the specific genomic regions of interest. Low density, on array capture hybridization is used for sequencing approaches. Such technology is not hypothesis neutral, as specific sequence information is required for the selection process.

A similar positive selection can be used for targeted resequencing. E.g. biotinylated RNA strands of high specificity for their complementary genomic targets can be used to extract DNA fragments for subsequent amplification and sequence determination. This form of complexity reduction is necessarily based on available sequence information and therefore not hypothesis neutral.

Sequencing of 16S rDNA or 16S rRNA sequences from mixed samples of microorganisms is i.a. employed for detection of rare species within these samples. By restricting the sequencing approach to a specific signature of microorganisms both complexity and information content are reduced. Frequently only phylogenetic information is obtained.

Tag-based identification of transcripts includes SAGE (Serial Analysis of Gene Expression) wherein sequence tags of defined length are extracted and sequenced. Since the initial creation of tag concatemers is a disadvantage for NGS, derived protocols are used omitting this step.

A related method is CAGE (Cap Analysis of Gene Expression). CAGE is intended to yield information on the 5' ends of transcripts and therefore on their respective transcription start sites. 5' cap carrying RNA molecules are selected before end-tags are extracted and sequenced.

Although only defined parts of the transcriptome are extracted for analysis SAGE and CAGE have their limitations because they do not allow for comprehensive segregation.

Several methods for interaction-specific enrichment of the genome exist. ChIP-Seq® is one of several approaches to extract sequences based on their respective affinities to specific proteins (frequently transcription factors). The associated DNA is immuno-precipitated, purified and sequenced. Only a very limited amount of questions is amenable to this approach.

Amplification-driven selection methods (like PCR and isothermal amplification) rely on the specific interaction of DNA oligonucleotides with their respective target DNA. E.g. bioinformatics-selected hexamers that serve as primers can be used for competitive amplification procedures. Such an approach does neither cover the full genome nor is the method scalable in terms of complexity reduction.

Another possibility is selective amplification of a subset of genomic DNA using a circularization approach. In this case a construct including a general primer pair motif which is flanked by two target-specific ends is used. Upon hybridization, ligation to the single stranded target sequence and amplification of the selected polynucleotide using a single primer is possible. Molecular Inversion Probe Capture (derived from initially termed "Padlock Probes") is used to select sub-sets of genomic DNA. This approach is not hypothesis neutral and limited in scalability.

Hypothesis neutral preparations of genomes that reduce the complexity of the sample have been disclosed in WO 2006/137734 and are based on AFLP technology (EP 0534858). For covering the whole genome a multitude of restriction enzymes must be used. This is laborious, introduces redundancy and still covers the genome only statistically as the pool of restriction fragments may or may not be completely sequenced due to the variability in restriction site distribution.

WO 2007/073171 A2 relates to a method of sequencing cDNA comprising a complexity reduction step by fragmenting cDNA by controlled endonuclease restriction enzymes. Thus, this method is dependent on the presence of proper endonuclease restriction sites in the cDNA sequence and always yields the same fragments for a given cDNA.

WO 2009/073629 A2 describes a shotgun sequencing methods to reduce redundancy in high genome coverage. Nucleic acids are fragmented mechanically or by ultrasound to produce a first shotgun library. The fragments of the first shotgun library are sequenced and the sequence reads are assembled. In a second step, target specific oligonucleotides are synthesized, specific for regions of interest such as locations of single nucleotide polymorphisms, and complexed with the target nucleic acids.

WO 2008/093098 A2 relates to a method for sequencing nucleic acids of at least two samples comprising randomly fragmenting the nucleic acids, ligating universal adaptors to the fragments and amplifying all nucleic acids for sequencing.

WO 2009/116863 A2 describes a method for identifying genomic DNA comprising the steps of generating a cDNA, an optional complexity reduction step, fragmenting the cDNA, optional size selection of the fragments, adaptor ligation, a further size and fragments selection steps, and binding to beads, among many further mandatory steps. This method is work intensive and simplification of complexity reduction for specific uses would be beneficial.

Therefore there is the need of methods that can provide for defined fractions of a nucleic acid sample and provide for means to improve sequencing processes, in particular for improving the assembly of sequences, and for the detection of rare nucleic acid samples e.g. in pools stemming from many organisms or genomes of high concentrations which reduce the chance to obtain sequences of rare nucleic acids.

SUMMARY OF THE INVENTION

Therefore, the present invention provides in a first aspect a method for the reduction of the complexity of nucleic acid pool(s), comprising
  providing a sample with one or more nucleic acid molecules,
  cutting the nucleic acid molecules by a random and/or sequence independent cutting step thereby obtaining a pool of nucleic acid fragments,
  amplifying one or more fragments of said nucleic acid molecules, wherein the one or more fragments constitute at least a fraction of all fragments of the nucleic acid molecules, and wherein the amplified or amplifying one or more fragments of said fraction are divided into different sub-pools, and wherein the fragments of each subpool comprise a common nucleic acid feature. Thus, for each subpool all fragments share the same nucleic acid feature. This same or common nucleic acid feature of course may differ between the separate subpools.

In this context, "amplified or amplifying" means that the one or more fragments, including amplified copies thereof, can be divided into the different subpools after and/or during an amplification reaction. The "fraction" refers to the portion or amount of the one or more fragments obtained in the cutting step that are further processed in the amplification and dividing step.

The inventive method can reduce the complexity of a sequence assembly by reducing the amount of sequence portions that have to be joined. In addition, rare (and even unknown) nucleic acids can be identified in the presence of highly abundant nucleic acids, since generally more nucleic acid fragments become detectable in the background of other fragments. Ultimately, such a method may facilitate the determination of rare genomes, or parts thereof, within a sample of abundant genomes. The method can further reduce the complexity of transcriptomic samples to such a degree that rare transcripts can be detected within the main competing signal of all other, possibly highly abundant transcripts. It is possible to measure quantitatively sequences and fragments thereof from the very rare to the highly abundant ones.

In particular the present invention provides for improved handling and sorting of nucleic acids contained in a pool of nucleic acids, e.g. for sorting or labelling purposes depending on a common nucleic acid feature of individual nucleic acids of the pool. In particular the present invention facilitates the separation of nucleic acids, each sharing said common nucleic acid feature into different subpools. Such a nucleic acid feature can e.g. be a shared sequence portion as will be elaborated more in detail below.

Central to the present invention is that in random or sequence independent cutting steps each nucleic acid molecule will be cut differently. This means that each nucleic acid molecule having the same sequence (being e.g. of a completely identical sequence or sharing a identical sequence portion) will be cut differently, thus resulting in a pool of different and very diverse fragments, sharing the same parent nucleic acid sequence. These fragments may have overlapping portions to fragments of different cutting events. In fact, this is an important criterion for sequence alignment if no prior sequence information is available to facilitate the alignment of sequence portions to a joined sequence. On the other hand, this random fragmenting sequence diversity greatly increases complexity of the sum of all fragments that have to be handled and eventually be sequenced. The present invention now reduces this complexity and helps to assign and sort the fragments into different subpools comprising a common nucleic acid feature. This is done by the amplification step, wherein fragments with the same parent nucleic acid sequence are divided into different subpools depending on the common nucleic acid feature. Of course not all fragments have to be sorted, e.g. for sequence determination approaches it is possible and also sufficient to only use a fraction, e.g. sequences or nucleic acid fragments of a defined length. Thus, it is also possible to only amplify and process a fraction of all fragments.

Usually during random fragmenting many diverse fragments are obtained. This diversity is still represented to some extend in the divided subpools—but of course with reduced complexity. The subpools thus usually contain a multitude of different fragments, at least more than one. Thus, the present invention can also be defined as a method for the reduction of the complexity of nucleic acid pool(s), comprising providing a sample with one or more nucleic acid molecules, cutting the nucleic acid molecules by a random and/or sequence independent cutting step thereby obtaining a pool of nucleic acid fragments, amplifying at least a fraction of said fragments, and wherein the amplified fragments, or during amplifying of said fragments the fragments of said fraction, are divided into different subpools, and wherein the fragments of each subpool all share the same nucleic acid feature and a sub-pool comprises more than one fragment. The subpools may comprise many diverse fragments such as at least 2, 3, 4, 5, 6, 7, 8, 9, 10, 20, 30, 40, 50 or more different fragments—of course all sharing the same nucleic acid feature.

The invention can also be used to improve the alignment of large numbers of individual sequencing reads to determine the sequence of nucleic acids and/or their copy number. Preferably the inventive method further comprises determining the sequences of the fragments for one or more subpools, further preferably comprising processing the sequences of a first sub-pool by aligning sequences or partial sequences of the fragments of the first sub-pool and join neighboring or overlapping sequences thereby obtaining a joined sequence, and optionally repeating the processing steps for one or more further subpools, wherein the sequences of the fragments of each further subpool are aligned and joined with the sequences of fragments and/or joined sequences of all previously processed subpool sequences, until a continuous sequence of at least one nucleic acid molecule of the sample is obtained.

When the length of the fragments of one or more subpools is above the length of the reads that are generated during the sequencing run, it is preferred that reads are also generated from within the fragments. Therefore the fragments of one or more subpools can be cut sequence dependent or independent by any means known to the art, or partial copies can be generated from such fragments that are sequenced. In another embodiment only partial sequences are generated during the sequencing run itself, e.g. by random priming each of the individual fragments of a subpool to start the sequencing. Therefore partial sequences of fragments of one or more subpools are generated. The alignment or assembly greatly benefits from first aligning or assembling (joining) such partial sequences within a subpool. Therefore the present invention also encompasses an embodiment wherein the fragments of at least one subpool are further cut, optionally sequence dependent or sequence independent, preferably into fragments of from 10 to 5000, more preferred 12 to 1000, further preferred of from 15 to 500 or 17 to 100 nucleotides length.

In preferred embodiments of the present invention the nucleic acid molecules are DNA molecules, in particular genomic DNA. It is further possible that the nucleic acid molecules are RNA, in particular RNA transcripts like mRNA, but also siRNA, snoRNA or microRNA. However, in preferred embodiments the nucleic acid molecules are large enough to yield a fragment size of at least 50, at least 80 or at least 100, at least 1,000 or at least 10,000 nucleotides.

Nucleic acids are linear polymers of single nucleotides. These molecules carry genetic information (see triplet code) or form structures which fulfill other functions in the cell (e.g. regulation). The nucleic acids which are related to this invention are deoxyribonucleic acid (DNA) and ribonucleic acid (RNA). The genome is the inheritable information encoded in DNA (or, for some viruses, RNA). The genome includes genes and non-coding sequences. Genomics is the study of the genomes of organisms.

The transcriptome is the set of all RNA molecules, or "transcripts," produced in cells. Unlike the genome, which is roughly fixed for a given cell line, the transcriptome varies with the kind of cell, tissue, organ and the stage of development. It can alter with external environmental conditions. Because it includes all RNA transcripts in the cell, the transcriptome reflects the genes that are being actively expressed at any given time, and it includes degradation phenomena such as transcriptional attenuation. Transcriptomics is the study of transcripts, also referred to as expression profiling.

The core principles of the method is similar for the analysis of genomic and transcriptomic data.

Genomic DNA is characterized through one or a few long molecules (chromosomes). This disclosed method describes how randomized sheared DNA can be sorted into a series of different subpools e.g. via termini selective amplification. Afterwards, the subpools are processed and sequenced.

The subpooling of transcript pools can be achieved through subpools with different additional information content. The gained benefits depend on the chosen methods.

A "nucleic acid molecule" according to the present invention shall be understood as a molecule having a certain sequence, shared by other nucleic acid molecules. In particular since the present invention aims at reducing the complexity of a pool of different cutting events (random fragmentation), the present invention aims at sorting and analyzing different cutting events of identical sequences comprised in nucleic acid molecules. This means that in the sample with one or more nucleic acid molecules multiple copies of said sequences are present. Such samples can e.g. comprise multiple copies of the same nucleic acid, comprise one nucleic acid with multiple copies of said sequence or mixtures thereof. The nucleic acid molecules of the present invention, in particular the common sequences thereof, may have an average nucleotide length. The nucleotide length as well as the copy number directly correlate with the complexity of the nucleic acid pool to be processed by the present invention. In a particular preferred embodiment a sufficient common nucleic acid feature is selected to facilitate a suitable complexity reduction. E.g. the number of subpools, each comprising at least one fragment, is created and a number of nucleic acid molecules in the sample times the fraction of the amplified fragments (the portion, e.g. percentage, of the fragments that are amplified from the original pool of nucleic acid fragments after the cutting step). In another embodiment it is preferred that a combined length of the fragments of at least one subpool is less than the average nucleotide length of the nucleic acid molecules (e.g. the sequence repeats of the randomly cut nucleic acid of the sample). It is particular beneficial if the size of the subpools is sufficiently small to allow an easier sequence determination and following sequence alignment procedure, in particular if the copy number of the original sample of the analyzed sequence is quite large.

The original sample can e.g. be a sample of cellular nucleic acid molecules as obtained after isolation, e.g. a sample of 1,000 diploid cells from one organism leads to 2,000 genome copies, which are all differently cut, or the sample may comprise nucleic acid molecules as obtained after e.g. PCR or any other amplification. The inventive segregation step for dividing the fragments of the amplified fraction into different subpools, systematically reduces the amounts of the fragments to be analysed and thus the complexity of the system. In preferred embodiments the numbers of subpools comprising at least one of the fragments is greater than the number of nucleic acid molecules in the sample and/or lower than the total amount of fragments per nucleic acid molecule in the sample.

To select the fraction of amplified fragments—or likewise for dividing (also referred to as segregation) fragments into different subpools during or after amplification, nucleic acid properties as distinctive nucleic acid feature which are directly or indirectly sequence related can be exploited. Such properties are for example the affinity to adsorbing materials like various column materials (e.g. silica gel) or the solubility in the presence of salts, polymers or other additives. In such indirect sequence related segregation the required information on the sample nucleic acids is limited, e.g. precipitation depends predominantly on length, the GC-content and secondary structures. The distinctive nucleic acid feature can be an adsorption or solubility property. Such properties and/or nucleic acid size are preferably used to (optionally) select a fraction to be amplified.

Alternatively or in addition, subpools or fractions can be generated through methods which utilize distinctive sequence information like i) partial internal or terminal sequences or ii) nucleic acid size. Preferably such sequence portions are used to divide fragments into subpools.

i) Using distinctive sequences is the most powerful segregation tool. E.g. a distinctive nucleic acid feature can be a partial sequence of the nucleic acids or their fragments stemming from the template nucleic acid molecules such as RNA or cDNA or (genomic) DNA (portions). The distinctive sequence can be a single nucleotide type (e.g. selected from A, T, U, G or C) or more at a specific position within the nucleic acids or fragments to be segregated. E.g. nucleotides can be segregated for the presence of one or more nucleotide types or sequences at either the 5' or 3' terminus or in a given distance from said terminus. On one hand an array of hybridization probes, which covers one or more sequence possibilities of said distinctive portion of the nucleic acid, can be used to create subpools. Even if subpools contain different nucleic acid fragments and some nucleic acid fragments will be present in several subpools, such a segregation approach already reduces the complexity of the original pool. After collecting all reads preferably the alignment algorithm ensures, that all nucleic acids display at least one subpool specific sequence.

Segregation by selecting for a distinctive nucleic acid feature like a distinctive sequence can be performed by either selecting such nucleic acids or fragments with the distinctive sequence or by specifically amplifying nucleic acids or fragments with said distinctive sequence and further utilizing these amplificates in the inventive method.

A preferred segregation method uses the sequence information of both termini, thus start and end site of the nucleic acid fragments. After termini-specific amplification and if the redundancy in the sequence specificity is zero (no mismatch allowed), then all subpools contain amplificates, e.g. PCR products, with exactly those termini. Hence, subpools can contain several transcripts but each transcript can only be presented in one subpool. By this means, the complexity of the alignment procedure is largely reduced.

ii) The nucleic acid size can be exploited to segregate the nucleic acid according to the number of nucleotides per transcript via electrophoresis techniques (gel or capillary electrophoresis), or other methods. The later alignment of the different reads per subpool can benefit from the boundary condition of a certain rather narrow size range.

It is also possible to first divide the nucleic acids into subpools due to a common nucleic acid feature and then perform the cutting step without or with the preferred further division of the fragments. Everything mentioned herein for dividing nucleic acids also applies for dividing the fragments and vice-versa.

The step of dividing a fragment into different subpools can be performed by any known means. This division is generally a qualitative division that leads to a quantitative reduction of the total number of fragments in each subpool. This means that substantially all fragments of a certain kind (sequence) are segregated into one particular subpool. "Substantially" means that a high efficiency of this division is preferred, e.g. about at least 90%, 95% or 99%, in particular preferred 99.9% of the fragments of one kind are segregated. "Dividing" as used herein also refers to specifically amplifying the fragments of one kind so that the segregated fragments (in total) constitute at least about 90%, 95%, 99% or at least 99.9% of the fragments of the subpool. In preferred embodiments this division step, also referred to as segregation step, can be in a sequence dependent manner or sequence independently. Likewise, selecting a fraction of the fragments for amplification can be sequence dependent or sequence independent. As mentioned above, sequence independent means include separation according to physical parameters like absorption or solubility. Sequence dependent means include segregation by a size of the fragments or for a specificity for certain sequence portions.

The phrase "comprising" shall be understood in the meaning of "having at least the following elements . . . " and is therefore open and does not exclude additional limitations. According to the invention each subpool comprises fragments with a common nucleic acid feature. This means that a subpool may comprise more than one, e.g. two, three, four or more, fragments with different nucleic acid features. Dividing (or also referred to as segregating) during or after amplification thus means that e.g. the fragments of more than one common nucleic acid feature can be selected or amplified for a given subpool (subpool mixture). The inventive complexity reduction can be achieved by performing the inventive selection for certain nucleic acid features, even if performed simultaneously. An example of obtaining subpool mixtures in one step according to the present invention is e.g. by multiplex PCR, using primers selecting for more than one nucleic acid features in one reaction. However, although there is sufficient complexity reduction in the generation of subpool mixtures, it is preferred that a subpool contains the fragments with one common nucleic acid feature used in the dividing or segregation step. Also preferred is when subpooling excludes the complete (undivided) pool of all nucleic acid molecule fragments.

In preferred embodiments of the present invention the step of dividing the fragments comprises selecting one or more fragment(s) with a common nucleic acid feature, preferably the presence of the same one or more nucleic acid type(s), selected from A, T, U, G or C at the same position for each subpool. In a particular preferred embodiment of the present invention the nucleic acid feature used for segregation is a given nucleotide type, preferably selected from any one of A, T, U, G, C, at a certain position in the fragment, preferably the position being within 100 nucleotides from either the 5' or 3' terminus of the fragments. Such methods that select for one specific nucleotides, e.g. to obtain a full length sequence source, are disclosed in the WO 2007/062445 (incorporated herein by reference). A nucleotide or nucleotide sequence used for segregation may comprise 1, 2, 3, 4, 5, 6, 7, 8, 9, 10 or more, e.g. up to 20 or up to 100 nucleotides. According to the present invention it is possible to amplify or select for specific fragments in a segregation step by using, e.g. a primer, which is specific for e.g. one end (either the 3' or 5' end) of the nucleic acid and containing one or more further nucleotides specificities which act to segregate the fragments according to the complementary nucleotides after a universal sequence portion on the primer. Such universal sequence portions, that allow a primer to hybridize specifically at the ends of nucleic acid fragments, can be introduced artificially e.g. by ligating oligonucleotides to the ends of all fragments after the fragmentation step. Of course two different universal sequences can be used, one specifying a 5' and one specifying a 3' end. Another method to introduce universal sequence portions is to copy the pool of fragments by primer extension using primers, that have on their 5' end the universal sequence portion and on their 3' end random nucleotides, such as random hexamers or nonamers that can randomly hybridize to fragments of the pool. In RNA analysis for instance such an approach can be used to introduce such a universal sequence during reverse transcription. In the segregation step the primers have a universal sequence portion, that is complementary to the ends, preferably ether to the 5' or 3' ends, of all fragments, and additional nucleotides that are selective for the next 1 to 100, preferably 1 to 10 nucleotides, e.g. the next 1, 2, 3, 4, 5, 6, 7, 8, 9, or 10 nucleotides. By using wobble nucleotides in the selective part of said primers it is also possible to select for specific nucleotides after these ends. Preferably the specific distinguishing nucleotides are within the first 100 nucleotides from either the 5' or 3' terminus of the fragment. It is of course also possible to use primers to select any internal region used to divide the fragments in the segregation step.

The same principle mentioned above for primers of course also applies for oligonucleotide probes which can be specific for such a distinguishing nucleotide type.

In cases where a universal sequence (e.g. of a linker) is present or has been introduced to allow for a primer to hybridize, the term terminal nucleotides or the word termini or terminal specifies nucleotides or sequence portions (ether 5' and/or 3') that are next to, and exclude, these universal sequence portions. These universal sequence portions can be added artificially as linkers or be a common hybridizing region mentioned above. Other universal sequences which are not used as nucleic acid feature in the segregation step can be natural repeat regions such as a poly-A tail of mRNA (or the corresponding poly-T stretch in its cDNA). Preferably, if a fragment contains such tails, a nucleic acid feature adjacent to the universal sequence is selected for segregation.

Preferably, the fragments are selected for common nucleotides within the 10 nucleotides next to the 5' and/or 3' terminus, preferably for one or more common 5' and/or 3' terminal nucleotide types.

These primers or probes preferably are used in combination with primers or probes which are selected for a different nucleic acid feature. Such primers can e.g. be used separately or sequentially to generate subpools specific for nucleic acid feature. Such primers or oligonucleotides used in a combination (i.e. "primer matrix") can e.g. be primers which have a universal part and a distinguishing part wherein the distinguishing part is e.g. A in the first primer, T in the second primer, G in the third primer and C in the fourth primer. Preferably, more than one nucleotide is used as the nucleic acid feature and the combination can e.g. be primers or oligonucleotide probes ending with AA, AT, AG, AC, TA, TT, TG, TC, GA, GT, GG, GC, CA, CT, CG, or CC (with the complementary nucleotides being distinctive nucleic acid features at a certain position in the fragments as criteria to separate the subpools). In a further preferred embodiment the nucleic acid feature contains 3 or more, e.g. 4, 5, 6, 7, 8, or more specific nucleotide types. Of course, due to the random nature of fragment generation, it is usually not necessary to determine all possible subpools. It can be sufficient to only select 1, 2, 3, 4, 5, 6, 7, 8, 9, 10, 11 or 12, seldom more, subpools after such a sequence dependent (or independent) segregation. Preferably 1% to 75% of the subpools are used for sequencing, preferably 5% to 50%. In a further preferred embodiment combinations of primers are oligonucleotides selecting for distinguishing nucleotides at both the 5' and/or 3' terminus, e.g. using both primers or probes being specific for the two or more 5' nucleotides and the two or more 3' nucleotides.

As mentioned above it is also possible to select for internal regions wherein it is also possible to use a combination of such a primer pair which selects for two nucleotide types on each side of the amplificate.

Usually, the samples used for the inventive method contain potentially diverse nucleic acid molecules of different origins or different sequence in diverse concentration ranges. These factors contribute to the complexity of the sample. Furthermore, fragmentation, usually of all nucleic acids, to provide short molecules suitable for NGS increases diversity and complexity of the sample pool. Modern sequencing approaches however, always contain a random factor which sequences are further processed. In particular next generation sequencing relates to generating sequence portions, called reads of small sequence fractions in the range of about 10 to several 100 nucleotides (nts) or even up to 500 nts, usually in the range of about 30 nts. In complex samples this has always the drawback that the transcript or genomic fragments of low concentration may be not sequenced in a parallel run in favour of fragments from transcripts or genomes of high copy numbers.

The invention concerns the preparation of nucleic acids suitable for downstream NGS. It is applicable for high-throughput sequencing of genomic and transcriptomic information. It provides major improvements for the unambiguous alignment of said reads.

It is also possible to ligate or join fragments to each other prior to sequencing—in particular if the fragments have been labeled to identify the fragment sequence in the ligated product. It is preferred that such joined fragments are interspersed by different sequence stretches that allow sequencing primers to prime consecutive rounds of sequencing.

The general principle is to reduce the complexity of a pool of nucleic acid fragments by sequencing smaller segregated portions after the inventive division into smaller portions called subpools. In a preferred embodiment all subpools together contain the whole information to be analyzed of the original pool. There are three main factors that contribute to the complexity of nucleic acid pools.

The first factor is determined by the combined length of the individual different sequences. Because the sequence is encoded through 4 bases (T and U are considered to represent the same information) the complexity increases with the variation, equal to the length to the power of four. However, sequences contain redundant information like repeats or any other kind of order. The total value of information is quantifiable using e.g. Shannon's information theory. While the raw information can only be deciphered through sequencing, the complexity which is introduced through repeats can be reduced by segregating the individual fragments before sequencing.

The second factor is determined by the number of different sequences within a sample. The complexity increases with the number of permutations, therefore with the factorial of different sequences. Two sequences have two possibilities to arrange, three sequences have six possibilities and so forth.

The third factor is the difference in copy numbers and to lesser degree the amount of precognition about these differences, e.g. if it is known that the difference is in the order of $1/1,000$. Each different sequence belongs to a group which is characterized of having one particular copy number. The level of distribution of these groups determines the complexity which is introduced through concentration differences.

The inventive segregation can help to distinguish different nucleic acids of the original sample pool or of the fragments. This segregation step can also be repeated once or more. Repetition herein shall not be interpreted that additional segregation steps have to be performed after the first segregation step which is of course one option—but also relates to pre-forming one or more segregation steps simultaneously. Thus, one or more subpools are generated and in each subpool specific nucleic acids are present (or enriched) which share a common feature and all other nucleic acids without that shared distinctive nucleic acid feature can be excluded from each pool (or at least are not enriched, e.g. by amplification).

These factors contribute directly to the difficulty of determining the correct sequence and concentration of all and in particular rare molecules within a sample. The general principle of the present invention is the constituting of subpools where these factors can be controlled, and simultaneously the complexity of the pool reduced, before reads are generated. Thus, the method simplifies the in-line sequence alignment to provide joined sequences.

The genome contains one or several long DNA molecules (Chromosomes). In general, the genome is one very long word written with four letters. To be able to sequence this long word smaller portions are necessary. The pool of fragments is divided into subpools. One way of creating a pool of polynucleotides is using one or more restriction enzymes to cut all copies of a genome (e.g. 1,000). In diploid eukaryotic cells two different genomic molecules for each chromosome pair contribute to the DNA pool. For example, if a genome has $10^9$ nucleotides (1 Gb) and restriction enzyme(s) would cut 1,000 genomes on average after 10 kb, then one pool with 100,000 different polynucleotides would be created with each polynucleotide being present 1,000 times too.

If only one restriction enzyme is used then the assembly the full length sequence is not possible because no overlaps occur for defining the order of the fragments. Therefore, at least 2 pools of the same DNA have to be cut, each with another restriction enzyme, and sequenced in order to assemble the full length sequence of the Genome (or Chromosomes). Therefore segregating strategies that depend on specific amplification (PCR) will cover only parts of the original pool. In most cases more than 2 pools of the same DNA must be processed through restriction enzymes, subpooled and sequenced to assemble a genome.

Therefore according to the present invention the cutting step is random and/or sequence independent, preferably by physical means, in particular preferred by sonication, shearing or elevated temperatures. This results in different fragments stemming from the same nucleic acid sequence. A fragment is considered a nucleic acid portion of shorter length than the complete nucleic acid molecule from which it is derived. In preferred embodiments the nucleic acid molecules are cut into fragments of from 10 to 200 000 nucleotides length, preferably of from 50 to 100 000 nucleotides length. Any ranges therein are of course also possible. The nucleic acid molecules can e.g. be cut into fragments of at least 10, at least 20, at least 30, at least 40, at least 50 nucleotides were up to 200 000 up to 150 000, up to 120 000, up to 100 000, up to 80 000, up to 70 000, up to 60 000, up to 50 000, up to 40 000, up to 30 000, up to 20 000, up to 10 000, up to 8000, up to 6000, up to 5000, up to 4000, up to 3000, up to 2000, up to 1000 nucleotides length. Subpools can be created through randomly cutting a DNA sample into fragments of approximate length, e.g. 10 kb (kilobases). Such cutting can be for instance a shearing process. For example, each of 1,000 genomes present in one sample would be cut into 100,000 polynucleotides of 10 kb (kilobases) length creating a pool of $10^8$ different polynucleotides.

If those random $10^8$ polynucleotides are segregated into 1,000 subpools, each would contain on average 100,000 of the 10 kb polynucleotides, on average one complete 1 Gb genome. No reduction in complexity would have been achieved because each short read must still be aligned to the 1 Gb.

In contrast, if the segregation would have been carried out into 10,000 subpools then the complexity of the alignment process of short read fragments within each subpool would be 10-fold reduced. Because, the sequences of the subpools are dispersed evenly throughout the genomes each subpool would contain only 10,000 of the 10 kb polynucleotides thus $\frac{1}{10}$ of the 1 Gb genomic sequence.

To achieve complexity reduction according to the present invention the number of subpools is preferably higher than the number of nucleic acid molecules in the sample. The amount of subpools that are needed for the same level of complexity reduction is direct proportional to the number of nucleic acid molecules. "A nucleic acid" relates to all molecules with a given sequence, i.e. a nucleic acid of the sample as well as all its copies obtained during amplification. According to this aspect the present invention provides a method for the reduction of the complexity of nucleic acid pool(s), comprising providing a sample with one or more nucleic acid molecules, cutting the nucleic acid molecules by a random and/or sequence independent cutting step thereby obtaining a pool of nucleic acid fragments, amplifying one or more fragments of said nucleic acid molecules, wherein the one or more fragments constitute at least a fraction of all fragments of the nucleic acid molecules, and wherein the one or more fragments of said fraction are divided into different subpools, each subpool comprising at least one fragment, wherein the number of subpools comprising at least one of the fragments is greater than the number of nucleic acid molecules in the sample times said fraction, and wherein the fragments of each subpool comprise a common nucleic acid feature. Of course, all preferred embodiments as described above or below also apply to this method. In principle the number of subpools should be greater than the number of different nucleic acid molecules. Of course, if only a fraction of the nucleic acid molecules is used (e.g. only a band of 9 kb to 11 kb as shown in the examples below) then the number of subpools may be reduced to achieve the same complexity reduction. The fraction (e.g. a certain percentage) of processed nucleic acids thus is a factor in the equation to determine a suitable number of subpools.

As example, starting with 1,000 genomes of 1 Gb and requiring a complexity reduction per subpool of 100, then 100,000 subpools must be created, each subpool containing on average only one thousand (1,000) 10 kb polynucleotides. Fortunately, not all subpools must be sequenced to cover the whole genome. In this example only little more than 100 subpools are required to have a higher than zero probability of seeing just enough tiny overlaps to be able to assemble the full length genome.

If i) the (e.g. 10 kb) fragments are randomly distributed and ii) the selection of the subpools was randomly chosen, then an ordinary probability function describes the chances of reading new sequences compare to reading sequences, or part thereof, which were already read before. To have a probability of close to one (>0.999) of reading once the entire genome, about 800 subpools need to be sequenced, with, 8× fold coverage.

Therefore, the complexity reduction is preferably not achieved through cutting the genome with restriction enzymes, but limiting the number of nucleic acid molecules in a subpool of fragments. Creating a number of subpools which is higher than the number of nucleic acid molecules within the starting pool of nucleic acids, the complexity within each subpool will be reduced.

The core of the invention is dividing or segregating nucleic acids to reduce the complexity of the task in aligning sequencing reads and foremost the ambiguity of doing so. Of course, in reality the challenge depends on many different aspects of the real natural system many of which relate to stochastic effects.

E.g. the segregation of a sequence entity after fragmentation into n equal subpools increases the uniqueness of the alignment of shorter sequence about n-fold, which depends on the degree of order within the sequence database and how the segregation occurred a mammalian genome has a total DNA of approximately $2.7 \times 10^9$ bp (e.g. "laboratory mouse" 2,716,965,481 bp. In case of a completely random sequence with the same size 12 bp long reads can have $4^{12}$ ($1.678 \times 10^7$) permutations if all four base-pairs are equally often represented. If every base-pair in the sequence is the start of a new permutation than the sequence can present $2.7 \times 10^9 - 11 \approx 2.7 \times 10^9$ permutations each permutation appears in average 161 times in such a genome.

As a consequence, the alignment of a random 12 bp sequence (r12bp) does not give a unique hit, instead a multialignment to 161 positions. The chance to align a particular read to the correct position is as little as $\frac{1}{161}$ and de facto none.

If the genome is divided into 256 subpools, then each contains $1.054 \times 10^7$ bp. The subpools may hold signatures like chemical identifier e.g. each fragment starting with a certain nucleotide type or sequence, lateral information in the sequencing machine or others. If the distribution obliges a Poisson-distribution, then the probability to find a certain number k of 12 bp read sequences in one subpool calculates to:

$$P(k) = \frac{\lambda^k e^{-\lambda}}{k!} \quad (1)$$

Therefore, a 12 bp read is not in 53% of the subpools, once in 34%, twice in 11% and three times in 2%, and so forth. The ratio 34/11/2 determines the probability to align a 12 bp read uniquely, to two or even 3 positions respectively.

However, the genetic information is not random, it contains a high degree of order. The bioinformatics survey of the mouse genome revealed that in 25-bp sequence fragments 80% are unique, 6% occur 2-10 times and 14% more than 10 times. The benefit of the inventive dividing segregating concerns those 20% which were not unique mapable before. 32-bp long sequence fragments increase the unique mapable window in the genome by just 5%, to 85%.

In other words, if reads are too short (for example, much shorter than 25 bp), then, statistically, they must have many repeats within the total sequence. If reads are reaching the length of close to 25 bp, than the statistically the uniqueness will become large enough to provide a very specific signature. However, such motives could have been copied during evolution and now the average length of the copied units determines the next significant reading length benchmark. If the read length crosses that length (e.g. 180 bp) most of those remaining reads will become objective assignable.

The value of alignment quality does not scale linear with the percentage coverage. That the last few percent are the hardest to obtain and the most valuable when attempting to determine the "whole" genomic sequence. The inventive approach specifically increases the chance of those remaining portions to provide full length sequences.

In preferred embodiments of the present invention sample comprises at least two, preferably at least 3 even more preferably at least 4, e.g. 5, 6, 7, 8, 9, 10 or more, at least 20, at least 50, at least 100, at least 1000 or at least 10 000 nucleic acid molecules. In further preferred embodiments of the invention sample comprises at least 2, 4, 5, 6, 7, 8, 9, 10 or more, at least 20, at least 50, at least 100, at least 1000 or at least 10 000 different nucleic acid molecules of different origin.

In preferred embodiments the fragments are divided into subpools wherein at least 10% of all subpools comprise the average amount of fragments of all subpools +/−50%. By employing a suitable segregation method for the given sample to divide the fragments evenly into the subpools the complexity reduction method is sufficiently used. Of course, further subpools may exist wherein fewer fragments are present, e.g. even empty subpools without any fragment of the original pool which can be used as control reference. In preferred embodiments at least 15%, at least 20%, at least 25%, at least 30%, at least 35%, at least 40% of all subpools comprise the average amount of fragments of all subpools +/−50%. This error margin of +/−50% is in preferred embodiment up to +/−50%, up to +/−45%, up to +/−40%, up to +/−35%, up to +/−30%, up to +/−25%, up to +/−20%.

In a further embodiment the fragments are divided in subpools wherein at least 10% of a subpool containing 6, 4, 3 or 2 or less fragments, preferably 1 fragment. Such a high dilution is in particular favorable for fragments that would be hard to assemble if further fragments would be present from the original pool.

In a further preferred embodiment the step of dividing the fragments comprises specifically amplifying the fragments from the original pool of nucleic acid fragments. In particular, the amplification is performed by nucleotide extension from a primer, preferably by PCR, in particular preferred wherein the amplification is performed by using primers which select for at least one, preferably at least two, in particular at least two adjacent, different nucleotides or at least three or more distinguishing nucleotides as described above after an unspecific primer portion whereby fragments are amplified which comprise the selected nucleotide as the nucleic acid feature specific for a subpool.

Fragments of different subpools may e.g. be distinguished by spatial separation or by attaching a subpool specific label to each fragment of a given subpool. It is then possible to distinguish fragments of different subpools during determining nucleotide sequences of fragments of combined pools. Alternatively nucleotide sequences of separate pools with or without attaching a label can be determined. This allows assigning fragment sequences to a subpool depending on a subpool-specific label and overlapping sequences with other fragments, thereby reducing complexity while determining the sequence of the nucleic acids.

Thus, in preferred embodiment subpool-specific labels or identifier are attached to the fragments. When fragments are further cut or partially copied of course also molecules that are derived from such subpool fragments can be labeled or identifiers can be attached. The subpool-specific labels can be nucleotides, which are preferably co-determined during sequence determination.

In further preferred embodiments the fragments, but also the nucleic acids in another step, of the original pool are divided into at least 2, preferably at least 3, at least 4, at least 5, at least 6, at least 7, at least 8 subpools during the segregation step, which fragments each share a different nucleotide characteristic for each subpool.

In preferred embodiments primers or probes used for selecting fragments in the segregation step are preferably immobilized on a solid surface, in particular a microarray or chip. The same type of segregation as described above for the distinguishing the nucleic acids can also be performed for distinguishing different fragments during the sequencing step.

The step of dividing the fragments into different subpools of course does not mean that each subpool has to be occupied, i.e. comprises one of the fragments. It is also possible that some of the subpools may remain empty, e.g. can be reference subpools. The dividing step, or segregation step is not necessarily absolute but can be relative. It also relates to dividing fragments through selective enrichment, i.e. amplification while non-selected fragments remain not amplified but still remain in the subpool sample.

In a further preferred embodiment of the present invention the number of occupied subpools is at least 5 times, preferably at least 10 times even more preferred at least 25 times, i.e. at least 30 times, at least 40 times, at least 50 times, at least 80 times, at least 100 times, at least 200 times, at least 300 times the number of nucleic acid molecules in the sample, in particular if these nucleic acid molecules are of a different sequence. The inventive method greatly benefits from increasing the amount of subpools in order to facilitate the alignment step of nucleic acid fragments that would align to multiple site of the original nucleic acid molecule, e.g. the genome. In preferred embodiments, the fragmented sample comprises at least one such sequence fragment that cannot be uniquely aligned.

As mentioned above it is possible to obtain the complete nucleic acid sequence after sequencing only one subpool and aligning, or joining the fragment sequences thereof. In preferred embodiments at least 2, at least 3, at least 4, at least 5, at least 8, at least 10, at least 12, at least 15, at least 20, at least 25, at least 30, at least 40, at least 45, at least 50, at least 60, at least 80, at least 100, at least 120 subpools are determined.

In further preferred embodiments the sequences of the fragments and/or joined sequences are aligned by determining common overlaps or by alignment to a template sequence when joining the sequences of neighbouring fragment sequences. It is both possible to obtain the joined complete sequence by either using a template, e.g. from a common nucleotide sequence data base and align the sequenced fragments to this template. On the other hand it is possible to join the sequences by determining overlapping sequences, e.g. of fragments which are cut in a different fashion and provide the connection information of 3' and 5' ends of different fragments.

It is a goal to sequence at least one nucleic acid molecule of the sample. Preferably at least 2, at least 4, at least 6, at least 8, at least 10, at least 15, at least 20, at least 30, at least 40, at least 100 or at least 150 nucleic acid molecules are sequenced.

In order to determine the sequence of the inventive fragments any common method known in the art is possible. Preferred sequencing methods comprise amplifying the fragments, or amplifying portions of these fragments and detecting each nucleotide type on each position with a label, a florescent nucleotide. Amplification sequencing approaches can e.g. be automated as on a chip or micro array or on beads.

In preferred embodiments the sample comprises at least 2 nucleic acid molecules with the same sequence, which are preferably cut at different sites thereby providing different fragments. In this case overlaps are obtained which can be used to join the sequences. Obtaining fragments which are cut at different sites can be e.g. by random, sequence independent cutting or by cutting using sequence independent endonucleases.

In preferred embodiments a sample comprises at least 2 nucleic acid molecules of different sequences, in particular of different origins or at different concentrations.

The present invention further illustrated by the following figures and examples without being limited thereto.

BRIEF DESCRIPTION OF THE DRAWINGS

FIGS. 3A-3C: Application of the general principle in a Next generation sequencing experiment.

DETAILED DESCRIPTION

The general workflow outlined here is as also used in Example 1.
Here, in step 6 each subpool contains three classes of fragments.
a) fragments that contain the L1 (linker 1) sequence. These sequences downstream of the L1 sequence (or L1 sequence part) depict the 5' start of the original fragments of step 3.
b) fragments that contain neither L1 nor L2 (linker 2) sequences (or L1-, L2 sequence parts). These fragments and their reads are from within the original fragments of step 3.
c) fragments that contain L2 (linker 2) sequences. The sequence upstream of the L2 sequence (or L2 sequence part) depict the 3' end of the original fragments of step 3.
The knowledge of the start and end sequences aids the assembly in step 9 as start and end sites of the fragments are defined.

The contig building of step 9 can be further advanced by assembling the contigs of step 9 (and the remaining reads) between the different subpools.

EXAMPLES

Example 1

Reducing the Complexity of a DNA Sample

Figure 1:
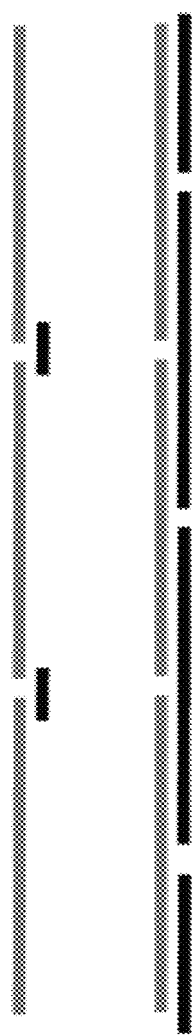
FIG. 1: coverage of a nucleic acid sequence by different fragment sizes.
Figure 2:
FIG. 2: General fragmentation and subpooling workflow, restricting the fragments of a polynucleotide sample to a certain number of subpools.
Figure 2:
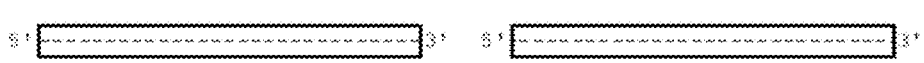
Figure 2:
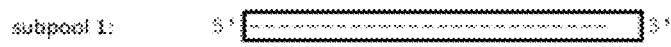
Figure 2:
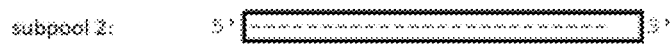
Figure 2:
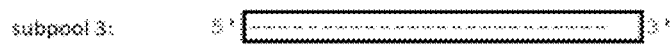
Figure 2:
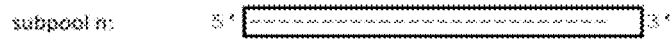
Figure 3B:
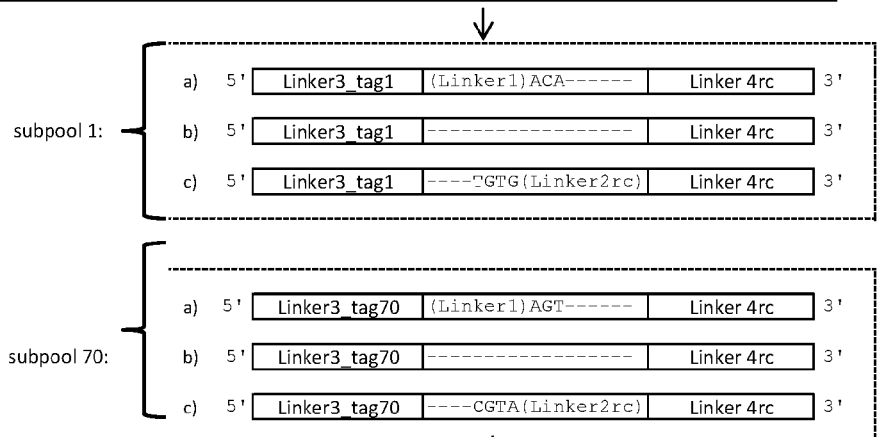
Figure 3C:
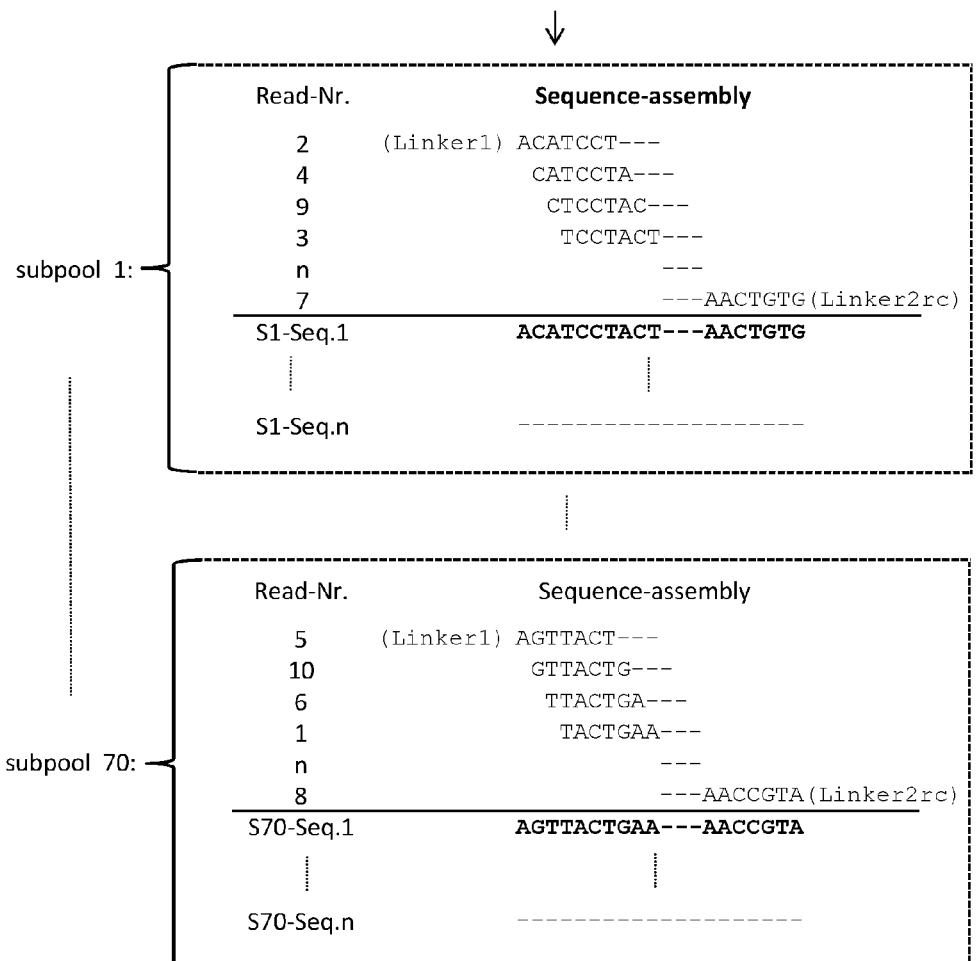

For a general outline of the workflow see also FIGS. 3A-3C. DNA was extracted from a sample containing $3 \times 10^5$ human diploid cells. The DNA in the sample was fragmented to an average fragment size of 10 kb by sonication.

The fragments were dephosphorylated on their 5' ends by alkaline phosphatase (to inhibit selfligation of the fragments in the following first ligation step). The fragments were briefly denatured at 95° C. and rapidly cooled on ice to provide single strands. Then a 5' phosphorylated single stranded Linker (L2rc; reverse complement to a L2 sequence) was ligated to the 3'-OH end of the fragments by T4 RNA ligase. After that the L2rc linked fragments were phosphorylated on their 5' end by polynucleotide kinase and a second Linker (L1) was ligated to the 5'-phosphate end of the L2rc linked fragments by T4 RNA ligase. Now about 1% of all fragments were ligated to the L1 and L2rc linker representing a DNA content equivalent to about $3 \times 10^3$ cells.

The ligated fragments were size separated through electrophoresis in an 0.5% agarose gel. Ligated fragments in the size range of 9-11 kb are cut out of the gel and purified. This fraction represents a DNA content equivalent to about $1.5 \times 10^2$ cells.

The 9-11 kb fraction was amplified by long PCR using the L1 and L2 sequences as primers to generate about 100 ng of PCR products.

In a segregating PCR, primers that contain the universal L1 and L2 sequences and on their 3'end a number of n selective nucleotides can reduce the complexity of the sample by a factor of 4', were n was the combined number of selective nucleotides of both primers. To be able to reduce the complexity of $1.5 \times 10^2$ cells below one haploid genome $4^n$ must be greater than $3 \times 10^2$. Therefore n must be at least 5. When n was 7, the complexity was reduced by a factor of about 54, or in other words each subpool would represent about ⅟₅₄th of a haploid genome equivalent.

Therefore a segregating PCR was carried out to create the subpools for a set A. 70 subpools of a 16.384 subpool matrix ($4^7$) were created by 70 individual PCR reactions containing each one of 70 possible primer combinations of 7 primers with L1-NNN (L1-ACA,-TAC,-CTT,-GAT,-CAA,-TTG,-AGT) and 10 primer with L2-NNNN (L2-CACA,-GTAC,-GCTT,-CGAT,-GCAA,-CTTG,-CAGT,-AGCT,-TCTG,-TACG). Set B consisted of a single sample that was amplified in a non-segregating PCR by using L1 and L2 primers only. In each PCR reaction 27 pg of DNA was amplified to about 500 ng.

The samples were then prepared for next generation sequencing on an Illumina Genome Analyzer II. Each of the PCR samples was fragmented into fragments which are on average 200-600 bp long. Linkers (L3, L4rc) were ligated to the ends of the fragments, which are used to bind the samples to the flow cell, allow for cluster generation and enable the hybridization of a sequencing primer to start the sequencing run. In addition for samples of set A each L3 linker contained a subpool specific sequence tag (barcode) to assign each sequencing read. Linker ligated fragments in a size range of 200-600 bp were size selected for sequencing. The 70 barcoded samples of set A were loaded onto 2 channels of the flow cell by pooling 35 samples per channel. The single sample of set B was loaded onto 2 channels of a second flow cell. After cluster generation on a cBot Instrument (Illumina Inc., USA), a 76 bp sequencing run was carried out on a GenomeAnalyzer II (Illumina Inc.) for each flow cell. About 15 million reads were generated per channel.

The reads of set A were segregated into the respective subpools according to the different channels and according to the different barcodes (sequence tags). In a first assembly contigs were built by first aligning reads within each subpool and then assembling contigs and remaining reads within all subpools together. In comparison, in a second assembly of set A contigs were built neglecting the sub-pool information. The average contig length of the first assembly was longer when contig building was done within each subpool first, compared to the second assembly, where the reads were not separated into subpools. In a third assembly contigs were built using reads of set B. In comparison the third assembly resulted in shorter contigs than the second or the first assembly.

Therefore a larger portion of the genome could be assembled when segregation was carried out. In addition in the first alignment in the majority of the cases contigs will come from one of the two haploid genomes allowing to distinguish between maternal or paternally derived sequences.

Example 2

Reducing the Complexity of an mRNA Sample mRNA was extracted from a sample containing 12.000 human cells that contain on average about 0.6 pg mRNA. 3.6 ng of mRNA could be recovered and was fragmented to an average fragment size of 100 bases.

A reverse transcription was carried out using random hexamers and reverse transcriptase to copy the cleaved mRNA fragments into cDNA. Second strand synthesis was carried out to remove the mRNA strand and synthesize a replacement strand to generate double stranded cDNA. cDNA ends were blunted by T4 DNA polymerase and Klenow DNA polymerase. Next an "A" base was added to the 3' end of the dsDNA fragments to create a single nucleotide overhang. Adapters (L5-L1-T and L6-L2-T) with a 3' "T" base overhang were then ligated to the fragments. Ligation products were size separated through gel electrophoresis. Ligates in the size range of 200(+/−25) bases were cut out of the gel and purified. This yields ligates with an cDNA insert content equivalent to an mRNA content of about 50 cells.

Adapter ligated cDNA was amplified by PCR using L5 and L6 sequences as primers to generate about 500 ng of PCR products.

Next two sets of samples were created. For set A the sample was segregated into n subpools and set B (where a single nonsegregating PCR was carried out) was analysed as a control.

In principle set A was created using primers that contain the universal L1 and L2 sequences and on their 3'end a number of n selective nucleotides, that can reduce the complexity of the sample by a factor of $4^n$, were n was the combined number of selective nucleotides of both primers. To be able to segregate the transcripts of 50 cells with a cellular copy number below 30 into different subpools, $4^n$ must be greater than 50×30. Therefore n must be at least 6. When n was 8, each subpool has a ⅟43 chance containing a transcript with a copy number below 30.

Therefore a segregating PCR was carried out to create sub-pools. 22 subpools of a 65.536 subpool matrix ($4^8$) are created by 22 individual PCR reactions containing each one of 22 possible primer combinations of 22 primers with L1-NNNN and 22 primers with L2-NNNN. In each PCR reaction 27 pg of DNA was amplified to about 500 ng.

Set B consists of a single control sample that was amplified in a non segregating PCR, using primers that contain only the universal L1 and L2 sequences.

The samples are then prepared for next generation sequencing on an Illumina Genome Analyzer II. Linkersequences (L3, L4) are added to the ends of the PCR products by 10 cycles of PCR using L3-L1 and L4-L2 primers, which are used to bind the samples to the flow cell, allow for cluster generation and enable the hybridization of a sequencing primer to start the sequencing run. The 22 samples of set A were loaded onto one channels of the flow cell by pooling the 22 samples per channel. Into a second channel the single sample of set B was loaded.

After cluster generation on a cBot Instrument (Illumina Inc., USA), a 36 bp sequencing run was carried out on a GenomeAnalyzer II (Illumina Inc.). About 15 million reads were generated per channel.

When analyzing the sequencing data sets, set A contained reads that are not part of set B. These reads represent low copy number transcripts. Therefore set A encompassed low copy number reads that cannot be detected without segregation.

Example 3

Reducing the Complexity of an mRNA Sample mRNA was extracted from a sample containing 24.000 human cells that contain on average about 1 pg mRNA, 12 ng of mRNA could be recovered and was fragmented to an average fragment size of 400 bases.

The fragments were dephosphorylated on their 5' ends by alkaline phosphatase (to inhibit selfligation of the fragments in the following first ligation step). The fragments were denatured at 92° C. for 30 seconds and rapidly cooled on ice to melt any secondary structure. Then a 5' phosphorylated single stranded Linker (L2rc+L6rc; 50 nts) was ligated to the 3'-OH end of the fragments by T4 RNA ligase. After that the L2rc+L6rc linked fragments were phosphorylated on their 5' end by polynucleotide kinase and a second Linker (L5+L1; 50 nts) was ligated to the 5'-phosphate end of the L2rc+L6rc linked fragments by T4 RNA ligase. Now about 1% of all fragments were ligated to the L5+L1 and L2rc+L6rc linker representing about 120 pg of mRNA that was equivalent to the mRNA content of about 120 cells.

A reverse transcription was carried out copying 120 pg of ligated mRNA fragments using a primer that contains L6 (reverse complement to L6rc) to generate cDNA.

120 pg of cDNA was amplified by PCR using the L5 and L6 as primers to generate about 500 ng of PCR products.

The PCR products are size separated through electrophoresis in an 6% polyacrylamide gel. Amplified fragments in the size range of about 475-525 bases were cut out of the gel and purified.

In a segregating PCR, primers that contain the universal L1 and L2 sequences and on their 3'end a number of n selective nucleotides can reduce the complexity of the sample by a factor of $4^n$, were n was the combined number of selective nucleotides of both primers. To be able to reduce the complexity of 120 cells below the mRNA content of one cell $4^n$ must be greater than 120. Therefore n must be at least 4. When n was 7, the complexity was reduced by a factor of about 136, or in other words each subpool would represent about ⅟136th of the mRNA content equivalent of a single cell.

A segregating PCR was carried out to create the subpools of a set A. 70 subpools of a 16.384 subpool matrix ($4^7$) are created by 70 individual PCR reactions containing each one of 70 possible primer combinations of 7 primers with L1-NNN (L1-ACA,-TAC,-CTT,-GAT,-CAA,-TTG,-AGT) and 10 primer with L2-NNNN (L2-CACA,-GTAC,-GCTT,-CGAT,-GCAA,-CTTG,-CAGT,-AGCT,-TCTG,-TACG). Set B consisted of a single sample that was amplified in a non-segregating PCR by using L1 and L2 primers only. In each PCR reaction 27 pg of DNA was amplified to about 500 ng.

The samples were then prepared for next generation sequencing on an Illumina Genome Analyzer II. Each of the PCR samples was fragmented into fragments which are on average 100 bp long. Adapters (50 bp) were ligated to the ends of the fragments, which are used to bind the samples to the flow cell, allow for cluster generation and enable the hybridization of a sequencing primer to start the sequencing run. In addition each adapter-pair contained a subpool specific sequence tag (barcode) to assign each sequencing read. Adapter ligated fragments in a size range of 175-225 bp were size selected for sequencing. The 70 barcoded samples were loaded onto 2 channels of the flow cell by pooling 35 samples per channel. After cluster generation on a cBot Instrument (Illumina Inc., USA), a 36 bp sequencing run is carried out on a GenomeAnalyzer II (Illumina Inc.). About 15 million reads are generated per channel.

The reads of set A were segregated into the respective subpools according to the different channels and according to the different barcodes (sequence tags). In a first assembly contigs were built by first aligning reads within each subpool and then assembling contigs and remaining reads within all subpools together. In comparison, in a second assembly of set A contigs were built neglecting the sub-pool information. The average contig length of the first assembly was longer when contig building was done within each subpool first, compared to the second assembly, where the reads were not separated into subpools. In a third assembly contigs were built using reads of set B. In comparison the third assembly resulted in shorter contigs than the second or the first.

Therefore longer mRNA sequences can be assembled using segregation.

Example 4

Improved Sequence Alignment

The inventive method divides a pool of random fragments into different subpools. This greatly enhances the alignment and assembly of short reads, such as they are returned by next generation sequencing platforms. In this example a simple model pool of fragments (160-305 bases long) is used to show the difference between an alignment of reads (4 bases long) within the whole pool of fragments and when such an alignment is done within each separate subpool. Ten random sequences between 160 and 305 were generated using a Random Letter Sequence Generator and arranged in a database, e.g. because of the small size it could be done in a spreadsheet, assembling the fragments of the model pool. All randomized numbers (e.g. fragment identifier) were generated using a randomizer.

TABLE 1

Short randomized sequences used as pool model.

| fragment | length | sequence |
|---|---|---|
| 1 | 202 | CATTACGTCCATATGAGTTCACGGTCCCTTGAACT<br>TTTATGGTAGGTGGTAGGCTCGGCGAATCTAGCTT<br>TGGAGCTTCGCCGGACTCAACAAGGTAAGGAGGAG<br>CATCGCTCTCTCGACCACTCAAGACGGGATATTAC<br>TTGTGTCAAGGAGATAATCGGAACTATTCTTTAGA<br>ATCCAGCTCGCCGAAATCGTCAGGCGA |
| 2 | 242 | CTAGCTTCGGTGTCATCCCGGAAGGCCCACGTTGT<br>GCGGCAATACTAGAGATAAAAGCGGCAAAGCTAAC<br>ACCGAAAGCCTATACTGGCTACCCGTCTCGTTCGG<br>TGGCACTAACTAGACTCCTCATCAGGCATAGGTGA<br>CCGCTCGCTCTCGTGCCAAGGTCTCCCGAGACTTC<br>CGAGATAGTAATAACTGAACATGGAGACCGGTATT<br>GTTAAGCTACATCAATTGTGGGCGAAACGAAC |
| 3 | 275 | CGTTCCGGCCTGAAGCTCGGGGATCCGGCCCCCCC<br>CTAACTTCGCTTTCTCAAACGTACAAATCAACCTT<br>ACTCGCATGCAGTAGATCTGCTTTGGGCCGTATCA<br>CACCTTCGGCTTGCCGTAAACCTGAATAGCAAATG<br>CGGGAGGGACTTTCCGTAATGTTGGGAATTACTTA<br>AACACATCTTCCGGGAGCACAATTTTCCGCCACTC<br>AACACGGTTTTCCTTGGTGCGTCTCATGCAATTC<br>TTCAGTGATGGGATACTTGGCAGGGATATC |
| 4 | 297 | CAGCCCGGACGCACTGAGATGATACGTGTTGAACC<br>GGCCTTCACTGTATATTATGCTCACGAGCCCTAGA<br>TTCATCAAAAAACAGGTACACTTCTCATCCTGACT |

TABLE 1-continued

Short randomized sequences used as pool model.

| fragment | length | sequence |
|---|---|---|
|  |  | ATACAGCTTTCAGTCATCCTACGATGGGAATCTAG<br>AGCCCATAGACATATATGAGCACACTACTCTTGGT<br>AACATCTCTTGTCACATACATTCGCCAATCTGAAT<br>CCTTTTCTGACAGCCAGTTCTCATGATCCAACACT<br>TAAGGATTTAGCATTACGGGGCGGGAGGAGAATCG<br>AATACTCGCCCACCGTC |
| 5 | 305 | ACTGGAGAGCACCGAACATACTCCTAGCCCGGGAT<br>GACAATGTCCTAACGCCACCCACTAAGGGTAAGGC<br>TCTAATTGGAAGGTAGTCCAAATACGCTCCATGAC<br>GAGCTTCGCTCTCAAGGCTCGCAGTCAGAACGTAT<br>CGACTATGCGACTCTAATTCCAAACCCAGAACCTG<br>AGCGAGGCAGTCGTTAGTTAATGACGCTTGCCGAG<br>AGAACAGTAAAGGAGTTCTTCGATGAGGTACTACG<br>ACATTCACATGTGTCATGGGTCGGTTAAGCATCTG<br>CGTGATTGATTCCGGGGGGTGTT |
| 6 | 297 | CAGCAGGTCGCATATATCAAAAGGGAAAGCCAGCT<br>CGCCTAGACGTCGTTCAATGGTAGGTACTTTAATT<br>TTTAGAGGGGCTTCCCCATGCTTTTGGAGATTGGC<br>CTATCGGTAGTGAGGATACCGGCCTCCACGCTGCG<br>TGATGAGCACAATCATTGTTCTCGGAGACGGAGGA<br>CCCGGAAGGTAACGAGCCCAAAGGTCATTCATACC<br>ATATAGGGCGTAACCTCATTTAGCGCGACTGACGT<br>GCAAGGGGCATCCGACCTGCGAGGAAGGGGCCTTG<br>GCTCTGTAGGATATAAT |
| 7 | 275 | TATCGAAAGCCCTAAGGATTTTTTTGGGGAATCG<br>ATTGTGTTAAGCAGGGACGGCTTCAAAATTCGTCT<br>AATAAGATTCTCTGGCCATTACCCTAACAGCGCCA<br>TACTCTATAGACGCACGCCTACCTTAGGCGCCTCC<br>CGTCCCCGGATCCGAGCTCCCAAAACCCAGCGACC<br>TCTTCATGCTAAGGACTTCATTTGGACCCGTCAGG<br>CACTGCTCCATGAAGAACGACATGAGGATTTGGAG<br>TATTAAAGGCTTAACACTGTAGCGCCACCG |
| 8 | 242 | GTGTCGTAACTGAGCGATACAGAACGACGCTGAGT<br>CATCGAGGCAAATGCGTCCACCCGCACCTGCGCAT<br>CCCATACAAGGTGGCACAACTTAGTAGGACTTATA<br>TGCGGACTTCACCGGTACGAGAAGAGTTGAAGACT<br>AAATTATGACGTGACAAACGAAAGAGTAAAACAAC<br>ATGCGTAGCTCTTCATGAAGCGGCAGAGCAAACCT<br>TGATTAAACCCCTTGATTGGCAACACTACACG |
| 9 | 202 | CGGTTACCCGGCGTTAGGCCTATGTACCGCCCGAC<br>GTACTTGCTAGGGGTCATACTACCGACGATCCCTG<br>CTAACAAAGAACAGTACCGGCTTTCCTTAACTACT<br>CAGTGCTACTAAAACTAGCATGAGGGTTGAGATCA<br>TCTCATCCAGTTGGGTCCAGCGCATGATTAATTGC<br>TTTACTCGCACTTTAATTCGGCTTCTA |
| 10 | 160 | GGAGGCACGACGAGTATCTAGTGTCTGCACGGGAC<br>TCCGGAGGACATTCCCTACAAGTTACCGGCGTCAG<br>TAGCAGCAAGACTGGTCTGTCTACCCCTGCCTGAC<br>AAAGTCTTTCTTGGATTTCGGACCGAAACTCGGCC<br>CAACATGCCATTGGCCATAT |

First, the fragments were ordered into 16 (4×4) different subpools according to their terminal bases (tab. 3).

Because one particular pool of fragments (all reads align to the blue print) is selected and any reading errors are excluded, a simple alignment algorithm (simple search function which provides the number of sequence matches) could be used to probe the fragment pool. It selects all reads that have a perfect k-mer match to the reference sequence (transcriptome). So, 24 permutations of 4 bp reads (without any base repeats like AATG) were taken and aligned, once against the entire model pool of fragments (tab. 2) and once against the segregated fragments within each subpool (tab. 3). The number of unique hits is shown in both tables in the right column.

TABLE 2

Compilation of number of possible 4 bp read alignments to the entire pool of fragments. None of the reads aligns uniquely.
24 permutation reads to 4 bp without repeats

| | fragment | ATGC | ATCG | AGTC | AGCT | ACTG | ACGT | TAGC | TACG | TGAC | TGCA | TCAG | TCGA |
|---|---|---|---|---|---|---|---|---|---|---|---|---|---|
| | 1 | 0 | 3 | 0 | 3 | 0 | 1 | 1 | 1 | 0 | 0 | 1 | 1 |
| | 2 | 0 | 0 | 0 | 3 | 2 | 1 | 1 | 0 | 1 | 0 | 1 | 0 |
| | 3 | 3 | 0 | 0 | 1 | 0 | 1 | 1 | 0 | 0 | 2 | 1 | 0 |
| | 4 | 1 | 1 | 1 | 1 | 2 | 1 | 1 | 3 | 2 | 0 | 1 | 1 |
| not | 5 | 1 | 1 | 3 | 1 | 1 | 1 | 1 | 2 | 3 | 0 | 1 | 2 |
| segregated | 6 | 1 | 1 | 0 | 1 | 1 | 2 | 1 | 0 | 1 | 1 | 0 | 0 |
| | 7 | 1 | 2 | 0 | 1 | 2 | 0 | 1 | 0 | 0 | 0 | 1 | 2 |
| | 8 | 3 | 1 | 1 | 1 | 1 | 1 | 1 | 1 | 2 | 0 | 0 | 1 |
| | 9 | 0 | 0 | 0 | 0 | 0 | 1 | 1 | 0 | 0 | 0 | 1 | 0 |
| | 10 | 1 | 0 | 1 | 0 | 1 | 0 | 1 | 0 | 1 | 1 | 1 | 0 |
| | hits per read | 11 | 9 | 6 | 12 | 10 | 9 | 10 | 7 | 10 | 4 | 8 | 7 |

| | fragment | GATC | GACT | GTAC | GTCA | GCAT | GCTA | CATG | CAGT | CTAG | CTGA | CGAT | CGTA | unique hits |
|---|---|---|---|---|---|---|---|---|---|---|---|---|---|---|
| | 1 | 0 | 1 | 0 | 2 | 1 | 0 | 0 | 0 | 1 | 0 | 0 | 0 | |
| | 2 | 0 | 2 | 0 | 1 | 1 | 3 | 1 | 0 | 3 | 1 | 0 | 0 | |
| | 3 | 2 | 1 | 1 | 0 | 1 | 0 | 2 | 2 | 0 | 2 | 0 | 4 | |
| | 4 | 1 | 1 | 1 | 2 | 1 | 0 | 1 | 2 | 2 | 4 | 1 | 0 | |
| not | 5 | 0 | 2 | 1 | 2 | 1 | 0 | 3 | 3 | 1 | 1 | 1 | 1 | |
| segregated | 6 | 0 | 1 | 1 | 1 | 2 | 0 | 1 | 0 | 1 | 1 | 0 | 1 | |
| | 7 | 1 | 1 | 0 | 1 | 0 | 1 | 3 | 0 | 0 | 0 | 1 | 0 | |
| | 8 | 0 | 3 | 1 | 1 | 1 | 0 | 2 | 0 | 0 | 2 | 1 | 2 | |
| | 9 | 2 | 0 | 3 | 1 | 2 | 3 | 2 | 3 | 2 | 0 | 1 | 1 | |
| | 10 | 0 | 2 | 0 | 1 | 0 | 0 | 1 | 1 | 1 | 1 | 0 | 0 | |
| | hits per read | 6 | 14 | 8 | 12 | 10 | 7 | 16 | 11 | 11 | 12 | 5 | 9 | 0 |

TABLE 3

Compilation of number of possible 4 bp read alignments to fragments segregated into 16 subpools according to the terminal nucleotides of the fragments. When the alignment is done within each subpool 69 of 224 reads align uniquely to a fragment.
24 permutation reads to 4 bp without repeats

| | subpool | fragment | ATGC | ATCG | AGTC | AGCT | ACTG | ACGT | TAGC | TACG | TGAC | TGCA | TCAG | TCGA |
|---|---|---|---|---|---|---|---|---|---|---|---|---|---|---|
| | A-/-A | | | | | | | | | | | | | |
| | A-/-T | 1 | 1 | 1 | 3 | 1 | 1 | 1 | 1 | 2 | 3 | 0 | 1 | 2 |
| | A-/-G | | | | | | | | | | | | | |
| | A-/-C | | | | | | | | | | | | | |
| | T-/-A | | | | | | | | | | | | | |
| | T-/-T | | | | | | | | | | | | | |
| | T-/-G | 7 | 1 | 2 | 0 | 1 | 2 | 0 | 1 | 0 | 0 | 0 | 1 | 2 |
| segregated | T-/-C | | | | | | | | | | | | | |
| into 16 | G-/-A | | | | | | | | | | | | | |
| subpools | G-/-T | 10 | 1 | 0 | 1 | 0 | 1 | 0 | 1 | 0 | 1 | 1 | 1 | 0 |
| | G-/-G | 8 | 3 | 1 | 1 | 1 | 1 | 1 | 1 | 1 | 2 | 0 | 0 | 1 |
| | G-/-C | | | | | | | | | | | | | |
| | C-/-A | 1, 9 | 0 | 3 | 0 | 3 | 0 | 2 | 2 | 1 | 0 | 0 | 2 | 1 |
| | C-/-T | 6 | 1 | 1 | 0 | 1 | 1 | 2 | 1 | 0 | 1 | 1 | 0 | 0 |
| | C-/-G | | | | | | | | | | | | | |
| | C-/-C | 2, 3, 4 | 4 | 1 | 1 | 5 | 4 | 3 | 3 | 3 | 3 | 2 | 3 | 1 |
| | | hits per read | | | | | | | | | | | | |

TABLE 3-continued

Compilation of number of possible 4 bp read alignments to fragments segregated into 16 subpools according to the terminal nucleotides of the fragments. When the alignment is done within each subpool 69 of 224 reads align uniquely to a fragment. 24 permutation reads to 4 bp without repeats

|  | subpool | fragment | GATC | GACT | GTAC | GTCA | GCAT | GCTA | CATG | CAGT | CTAG | CTGA | CGAT | CGTA | unique hits |
|---|---|---|---|---|---|---|---|---|---|---|---|---|---|---|---|
|  | A-/-A |  |  |  |  |  |  |  |  |  |  |  |  |  |  |
|  | A-/-T | 1 | 0 | 2 | 1 | 2 | 1 | 0 | 3 | 3 | 1 | 1 | 1 | 1 | 13 |
|  | A-/-G |  |  |  |  |  |  |  |  |  |  |  |  |  |  |
|  | A-/-C |  |  |  |  |  |  |  |  |  |  |  |  |  |  |
|  | T-/-A |  |  |  |  |  |  |  |  |  |  |  |  |  |  |
|  | T-/-T |  |  |  |  |  |  |  |  |  |  |  |  |  |  |
|  | T-/-G | 7 | 1 | 1 | 0 | 1 | 0 | 1 | 3 | 0 | 0 | 0 | 1 | 0 | 9 |
| segregated into 16 subpools | T-/-C |  |  |  |  |  |  |  |  |  |  |  |  |  |  |
|  | G-/-A |  |  |  |  |  |  |  |  |  |  |  |  |  |  |
|  | G-/-T | 10 | 0 | 2 | 0 | 1 | 0 | 0 | 1 | 1 | 1 | 1 | 0 | 0 | 12 |
|  | G-/-G | 8 | 0 | 3 | 1 | 1 | 1 | 0 | 2 | 0 | 0 | 2 | 1 | 2 | 12 |
|  | G-/-C |  |  |  |  |  |  |  |  |  |  |  |  |  |  |
|  | C-/-A | 1, 9 | 2 | 1 | 3 | 3 | 3 | 3 | 2 | 3 | 3 | 0 | 1 | 1 | 5 |
|  | C-/-T | 6 | 0 | 1 | 1 | 1 | 2 | 0 | 1 | 0 | 1 | 1 | 0 | 1 | 14 |
|  | C-/-G |  |  |  |  |  |  |  |  |  |  |  |  |  |  |
|  | C-/-C | 2, 3, 4 | 3 | 4 | 2 | 3 | 3 | 3 | 4 | 4 | 5 | 7 | 1 | 4 | 4 |
|  |  | hits per read |  |  |  |  |  |  |  |  |  |  |  |  | 69 |

This example experiment shows, that i) none of the 24 probed reads gave one unique hit when trying to align reads to the entire pool of fragments. The number of total hits was 224. The most unique read aligned matched 4 different fragments.

ii) After segregation into 7 subpools, here according to the molecule ends (first and last nucleotide), 69 (31%) of the reads could already be aligned uniquely.

Even without having a blue print the same principle applies. In the first case none of the investigated reads will belong to a unique position in the pool, whereas 31% of the reads will have one unique position in their host subpool.

What is claimed is:

1. A method for the reduction of the complexity of nucleic acid pool(s), comprising:
   a) providing a sample with one or more nucleic acid molecules,
   b) cutting the nucleic acid molecules by a random and/or sequence independent cutting step thereby obtaining a pool of nucleic acid fragments,
   c) linking the pool of fragments to a common linker,
   d) providing a plurality of different amplification primer sets, wherein each amplification primer set is configured to selectively amplify linked fragments, wherein the different amplification primer sets differ in that they are configured to amplify a different nucleic acid feature outside of said common linker, wherein the amplification primer sets are provided separated from the other amplification primer sets, and
   e) selectively amplifying a fraction of said linked fragments with said plurality of different amplification primer sets to form a plurality of different subpools, with each subpool being the product of amplification by a separate different amplification primer set, amplification products of each subpool sharing the different nucleic acid feature, wherein at least one subpool comprises more than one different fragment.

2. A method for the reduction of the complexity of nucleic acid pool(s), comprising:
   a) providing a sample with one or more nucleic acid molecules,
   b) cutting the nucleic acid molecules by a random and/or sequence independent cutting step thereby obtaining a pool of nucleic acid fragments, and
   c) linking the pool of fragments to a common linker,
   d) providing a plurality of different amplification primer sets, wherein each amplification primer set is configured to selectively amplify linked fragments wherein the different amplification primer sets differ in that they are configured to amplify a different nucleic acid feature outside of said common linker wherein amplification primer sets are provided separated from other amplification primer sets, and
   e) selectively amplifying one or more linked fragments of said nucleic acid molecules with said plurality of different amplification primer sets to form a plurality of different subpools, with each subpool being the result of amplification by a separate and different amplification primer set, amplification products of each subpool sharing different nucleic acid feature, wherein the one or more fragments constitute at least a fraction of all fragments of the nucleic acid molecules.

3. The method of claim 1, characterized in that the cutting step is by a physical means, optionally by sonication, shearing or elevated temperature.

4. The method of claim 2, characterized in that the sample comprises at least two, or optionally at least three, nucleic acid molecules.

5. The method of claim 1, characterized in that the nucleic acid molecules are cut into fragments of from 10 to 200000 nucleotides length or from 50 to 100000 nucleotides in length.

6. The method of claim 1, characterized in that the fragments are divided into subpools wherein at least 10% of all subpools comprise the average amount of fragments of all subpools +/−50%.

7. The method of claim 1, characterized in that the number of occupied subpools is at least 5 times the number of nucleic acid molecules in the sample.

8. The method of claim 1, characterized in that the plurality of different subpools are formed by selecting fragments with the shared nucleic acid feature, at the same position, for each subpool, wherein selecting comprises amplifying fragments with the nucleic acid feature.

9. The method of claim 8, characterized in that the fragments are selected for common nucleotides within the 10 nucleotides next to the 5' and/or 3' terminus, optionally for one or more common 5' and/or 3' terminal nucleotide types.

10. The method of claim 1, characterized in that the fragments of at least one subpool are further cut, optionally sequence dependent or sequence independent, optionally into fragments of from 10 to 5000, 12 to 1000, 15 to 500, or 17 to 100 nucleotides in length.

11. The method of claim 1, characterized in that the sequences of fragments of at least one, or optionally at least two, or optionally at least three subpools are determined.

12. The method of claim 11, further comprising processing the sequences or partial sequences of a first sub-pool by aligning sequences of the fragments of the first sub-pool and join neighbouring or overlapping sequences thereby obtaining a joined sequence, and optionally repeating the processing steps for one or more further subpools, wherein the sequences of the fragments of each further subpool are aligned and joined with the sequences of fragments and/or joined sequences of all previously processed subpool sequences, until a continuous sequence of at least one nucleic acid molecule of the sample is obtained, optionally wherein the sequences of the fragments and/or joined sequences are aligned by determining common overlaps or by alignment to a template sequence and joining the sequences of neighbouring fragment sequences.

13. The method of claim 1, characterized in that the sample comprises at least two nucleic acid molecules with the same sequence, which are optionally cut at different sites thereby providing different fragments, or the sample comprises at least two nucleic acid molecules with different sequences.

14. The method of claim 1, comprising labeling the fragments with a subpool-specific identifier prior to determining their sequence.

15. A method for the reduction of the complexity of nucleic acid pool(s), comprising:
   a) providing a sample with one or more nucleic acid molecules,
   b) cutting the nucleic acid molecules by a random and/or sequence independent cutting step thereby obtaining a pool of nucleic acid fragments,
   c) linking the pool of fragments to a common linker,
   d) providing a plurality of different amplification primer sets, wherein each amplification primer set is configured to selectively amplify linked fragments wherein the different amplification primer sets differ in that they are configured to amplify a different nucleic acid feature outside of said common linker wherein the amplification primer sets are provided separated from the other amplification primer sets, and
   e) selectively amplifying one or more linked fragments of said nucleic acid molecules with said plurality of different amplification primer sets to form a plurality of different subpools, with each subpool being the product of amplification of a separate and different amplification primer set, amplification products of each subpool sharing the different nucleic acid feature, wherein the one or more fragments constitute at least a fraction of all fragments of the nucleic acid molecules, each subpool comprising at least one fragment,
   wherein the number of subpools comprising at least one of the fragments is greater than the number of nucleic acid molecules in the sample times said fraction, and wherein the shared nucleic acid feature is optionally further defined as in claim 3.

16. A method for the reduction of the complexity of nucleic acid pool(s), comprising:
   a) providing a sample with one or more nucleic acid molecules,
   b) cutting the nucleic acid molecules by a random and/or sequence independent cutting step thereby obtaining a pool of nucleic acid fragments, and
   c) linking the pool of fragments to a common linker,
   d) providing a plurality of different amplification primer sets, wherein each amplification primer set is configured to selectively amplify linked fragments wherein the different amplification primer sets differ in that they are configured to amplify a different nucleic acid feature outside of said common linker, and
   e) selectively amplifying at least a fraction of said linked fragments with said plurality of different amplification primer sets to form a plurality of different subpools, with each subpool being the product of amplification of a separate and different amplification primer set, amplification products of each subpool sharing the different nucleic acid feature, wherein the fragments of each subpool all share the same nucleotide type at the same position from either terminus as the shared nucleic acid feature and a subpool comprises more than one different fragment, optionally further defined as in claim 3.

17. The method of claim 8, characterized in that the common nucleic acid feature is the presence of the same one or more nucleic acid type(s) selected from A, G, T, U, or C, at the same position.

18. The method of claim 1, characterized in that each of the different nucleic acid features are intrinsic to one or more nucleic acid molecules in the sample.

* * * * *